(12) United States Patent
Naqvi et al.

(10) Patent No.: US 9,170,218 B2
(45) Date of Patent: Oct. 27, 2015

(54) NITROGEN DETECTION IN BULK SAMPLES USING A D-D REACTION-BASED PORTABLE NEUTRON GENERATOR

(71) Applicant: KING FAHD UNIVERSITY OF PETROLEUM AND MINERALS, Dhahran (SA)

(72) Inventors: Akhtar Abbas Naqvi, Dhahran (SA); Muhammad Ashraf Gondal, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/104,830

(22) Filed: Dec. 12, 2013

(65) Prior Publication Data

US 2015/0168319 A1 Jun. 18, 2015

(51) Int. Cl.
*G01N 23/222* (2006.01)
*G01N 23/221* (2006.01)

(52) U.S. Cl.
CPC ............ *G01N 23/222* (2013.01); *G01N 23/221* (2013.01)

(58) Field of Classification Search
CPC ...... G01T 1/167; G01N 23/222; G01N 23/221
See application file for complete search history.

(56) References Cited

U.S. PATENT DOCUMENTS

| | | | |
|---|---|---|---|
| 6,207,953 B1 | 3/2001 | Wilson | |
| 6,495,837 B2 | 12/2002 | Odom et al. | |
| 7,796,720 B1 | 9/2010 | Rubbia | |
| 7,897,934 B2 | 3/2011 | Sved | |
| 8,288,734 B2 | 10/2012 | Norris | |
| 2002/0175288 A1* | 11/2002 | Taleyarkhan | 250/358.1 |
| 2010/0301226 A1 | 12/2010 | Lacy | |
| 2014/0284490 A1* | 9/2014 | Caffrey et al. | 250/390.04 |

* cited by examiner

*Primary Examiner* — David Porta
*Assistant Examiner* — Hugh H Maupin
(74) *Attorney, Agent, or Firm* — Oblon, McClelland, Maier & Neustadt, L.L.P.

(57) ABSTRACT

A D-D portable neutron generator-based PGNAA setup is designed and tested for nitrogen concentration measurements in bulk samples. The PGNAA set up response was tested through 2.50 MeV and 2.52 MeV nitrogen prompt gamma ray yield measurements and indicates that the excellent performance of the portable neutron generator-based PGNAA setup can be used for detection of elements with low thermal neutron capture cross-section.

13 Claims, 9 Drawing Sheets

NITROGEN DETECTION IN BULK SAMPLES USING A D-D REACTION-BASED PORTABLE NEUTRON GENERATOR

BACKGROUND OF THE INVENTION

1. Technical Field

The present invention relates to a D-D portable neutron generator apparatus using prompt gamma-ray neutron activation analysis (PGNAA) comprising a portable neutron generator, a high density polyethylene (HDP) cylinder, a cylindrical gamma ray detector, a lead shield, and a neutron shield.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The prompt gamma-ray neutron activation analysis (PG-NAA) technique is widely used for in situ elemental analysis of bulk samples in several scientific disciplines including environmental, industrial, and health sciences (R. L. Paul and R. M. Lindstrom, "Prompt gamma-ray activation analysis: fundamentals and applications," *Journal of Radioanalytical and Nuclear Chemistry*, vol. 243, no. 1, pp. 181-189, 2000 incorporated herein by reference in its entirety). Its area of application ranges from quality-control tasks in mining and environmental (D. L. Chichester, J. D. Simpson, and M. Lemchak, "Advanced compact accelerator neutron generator technology for active neutron interrogation field work," *Journal of Radioanalytical and Nuclear Chemistry*, vol. 271, no. 3, pp. 629-637, 2007; Z. Idiri, H. Mazrou, A. Amokrane, and S. Bedek, "Characterization of an Am—Be PGNAA set up developed for in situ liquid analysis: application to domestic waste water and industrial liquid effluents analysis," *Nuclear Instruments and Methods in Physics Research B*, vol. 268, no. 2, pp. 213-218, 2010; A. A. Naqvi, M. S. Al-Anezi, Z. Kalakada et al., "Response tests of a LaCl3:Ce scintillation detector with low energy prompt gamma rays from boron and cadmium," *Applied Radiation and Isotopes*, vol. 70, no. 5, pp. 882-887, 2012; A. A. Naqvi, Z. Kalakada, M. S. Al-Anezi et al., "Low energy prompt gamma-ray tests of a large volume BGO detector," *Applied Radiation and Isotopes*, vol. 70, no. 1, pp. 222-226, 2012—each incorporated herein by reference in its entirety) and building construction industries (R. A. Livingston, M. Al-Sheikhly, and A. B. Mohamed, "Numerical simulation of the PGNA signal from chlorine diffusion gradients in concrete," *Applied Radiation and Isotopes*, vol. 68, no. 4-5, pp. 679-682, 2010—incorporated herein by reference in its entirety) to contraband detection for homeland security in concealed containers (A. Buffler and J. Tickner, "Detecting contraband using neutrons: challenges and future directions," *RadiationMeasurements*, vol. 45, no. 10, pp. 1186-1192, 2010; E. H. Seabury, "PINS measurements of explosive stimulants for cargo screening," Report no. INL/EXT-08-14053, Idaho National Laboratory, Idaho Falls, Id., USA, 2008; E. H. Seabury, J. C. Wharton, and A. J. Caffrey, "Response of a LaBr3:Ce detector to 2 11 MeV gamma rays," Report no. INL/CON-06-11300, Idaho National Laboratory, Idaho Falls, Id., USA, 2006; E. H. Seabury and A. J. Caffrey, "Explosive detection and identification by PGNAA," Report no. INEEL/EXT-04-02475, Idaho National Laboratory, Idaho Falls, Id., USA, 2004; D. Strelllis and T. Gozani, "Classifying threat with a 14 MeV neutron interrogation system," *Applied Radiation and Isotopes*, vol. 63, no. 5-6, pp. 799-803, 2005—each incorporated herein by reference in its entirety). Prompt gamma rays can be excited in samples via thermal neutron capture (nth, $\gamma$) reaction and fast neutron inelastic scattering (n, n$\acute{}$ $\gamma$) reactions.

Former reaction is used for elements with appreciable thermal neutrons capture cross-sections, while later reaction is used for elements with negligible thermal neutron capture cross-section. Therefore prompt gamma rays produced via 14 MeV neutron inelastic scattering from elements are used to measure C, N, and O concentrations in bulk samples (P. A. Dokhale, J. Csikai, and L. Ol$\hat{}$Ah, "Investigations on neutron-induced prompt gamma ray analysis of bulk samples," *Applied Radiation and Isotopes*, vol. 54, no. 6, pp. 967-971, 2001; P. A. Dokhale, J. Csikai, and L. Ol$\hat{}$Ah, "Investigations on neutron-induced prompt gamma ray analysis of bulk samples," *Applied Radiation and Isotopes*, vol. 54, no. 6, pp. 967-971, 2001; C. Eleon, B. Perot, C. Carasco, D. Sudac, J. Obhodas, and V. Valkovic, "Experimental and MCNP simulated gamma-ray spectra for the UNCOSS neutron-based explosive detector," *Nuclear Instruments and Methods in Physics Research A*, vol. 629, no. 1, pp. 220-229, 2011; A. V. Kuznetsov, A. V. Evsenin, I. Y. Gorshkov, O. I. Osetrov, and D. N. Vakhtin, "Detection of buried explosives using portable neutron sources with nanosecond timing," *Applied Radiation and Isotopes*, vol. 61, no. 1, pp. 51-57, 2004; A. A. Naqvi, F. A. Al-Matouq, F. Z. Khiari, A. A. Isab, Khateebur-Rehman, and M. Raashid, "Prompt gamma tests of LaBr3:Ce and BGO detectors for detection of hydrogen, carbon and oxygen in bulk samples," *Nuclear Instruments and Methods in Physics Research A*, vol. 684, pp. 82-87, 2012; B. Perota, C. Carasco, S. Bernard et al., "Measurement of 14 MeV neutron-induced prompt gamma-ray spectra from 15 elements found in cargo containers," *Applied Radiation and Isotopes*, vol. 66, no. 4, pp. 421-434, 2008—each incorporated herein by reference in its entirety). Due to interference of weak intensity nitrogen prompt gamma rays with oxygen gamma rays, detection of nitrogen in bulk samples is a tedious task in 14 MeV neutron inelastic scattering studies. In spite of small thermal neutron capture cross-section, nitrogen can also be detected via prompt gamma ray studies in thermal neutron capture reaction studies (A. Favalli, H.-C. Mehner, V. Ciriello, and B. Pedersen, "Investigation of the PGNAA using the LaBr3 scintillation detector," *Applied Radiation and Isotopes*, vol. 68, no. 4-5, pp. 901-904, 2010; A. T. Farsoni and S. A. Mireshghi, "Design and evaluation of a TNA explosive-detection system to screen carry-on luggage," *Journal of Radioanalytical and Nuclear Chemistry*, vol. 248, no. 3, pp. 695-697, 2001—each incorporated herein by reference in its entirety). Conventionally, nitrogen detection in bulk sample via thermal neutron capture is carried out using a 252Cf neutron source.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

In one embodiment of the present invention a D-D neutron generator-based prompt gamma-ray neutron activation analysis apparatus is used to detect nitrogen in bulk samples.

In another embodiment, the D-D neutron generator-based prompt gamma-ray neutron activation analysis apparatus is portable.

In another embodiment the D-D portable neutron generator-based prompt gamma-ray neutron activation analysis apparatus includes a portable neutron generator, a high density polyethylene cylinder, a cylindrical gamma ray detector and a lead shield and neutron shield configured adjacent to the sides of the cylindrical gamma ray detector.

In another embodiment the portable neutron generator may be a pulsed neutron generator.

In another embodiment the high density polyethylene cylinder may be configured to be a high density polyethylene cylindrical slab that is inserted between the portable neutron generator and the sample.

In another embodiment the high density polyethylene cylinder may be configured to be a high density polyethylene cylinder which encloses the sample and is configured to a high density polyethylene slab configured to the portable neutron generator.

In another embodiment the high density polyethylene cylinder may be configured to be a high density polyethylene moderator cylinder which encloses the sample and is configured adjacent to the neutron generator.

In another embodiment the cylindrical gamma ray detector may be a bismuth germinate detector.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Referring now to the drawings, wherein like reference numerals designate identical or corresponding parts throughout the several views.

In one embodiment of the invention nitrogen is detected in bulk samples via thermal neutron capture using a D-D reaction-based portable neutron generator. Thermal neutrons were produced in conjunction with 2.5 MeV fast neutrons from a portable neutron generator using the high density polyethylene moderators.

In another embodiment, a portable D-D reaction based pulsed neutron generator model MP320, from Thermo-Fisher, USA, is used for the elemental analysis of bulk samples for prompt gamma studies. The Thermo Scientific MP 320 is a lightweight, portable neutron generator suited for field or laboratory applications. It has very low power requirements and may be operated from battery or vehicle power sources. It contains a Deuterium-Deuterium (DD) neutron tube. The portable neutron generator preferably has a weight of less than 20 Kg, more preferably less than 15 Kg, less than 12 kg or less than 10 Kg. The portable neutron generator preferably has a power consumption of 10-100 µA, preferably 20-80 µA, 30-70 µA, or about 60 µA. The pulse rate of the neutron generator is in the range of 250 Hz to 20 kHz continuous and runs on preferably less than 50 w power, preferably less than 40 w. The neutron generator also has a pulse rise and pulse fall time of less than 1.4 µsec and a minimum pulse width of 5 µsec.

A thermal neutron capture-based prompt gamma ray neutron activation analysis system/apparatus includes the portable neutron generator. The setup was tested with nitrogen concentration measurement in bulk samples of explosive and narcotics proxy material. In one embodiment, the application of nitrogen detection for explosive detection concealed in cargo containers uses the PGNAA technique, and the setup of the neutron generator may be modified.

In another embodiment, the cylindrical moderator may be replaced with a moderator-slab inserted between the neutron generator and the object under investigation. In one embodiment the moderator slab is a polyolefin slab. The polyolefin includes but is not limited to polyethylene (PE), high-density polyethylene (HDP), medium density polyethylene (MDPE), linear low-density polyethylene (LLDPE), cross-linked polyethylene (PEX), low-density polyethylene (LDPE), polypropylene (PP), polymethylpentene (PMP), polybutene-1 (PB-1) or other poly-alpha olefins. Preferably, the polyolefin is high-density polyethylene. This reduces the data acquisition time because sample size is much larger than conventional laboratory samples and the detector covers a much larger solid angle.

Figure 1A:
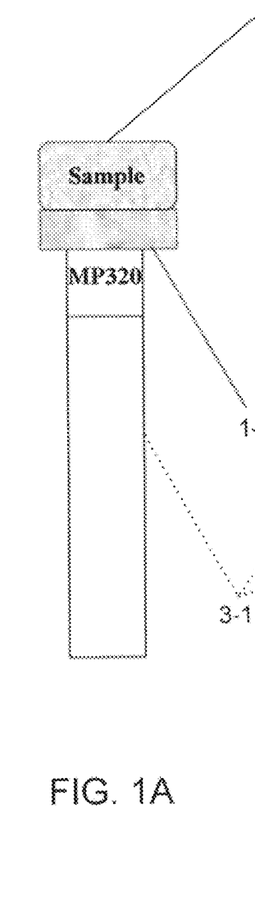
FIGS. 1A-1C show three different source-moderator sample geometries of the PGNAA setup.

Monte Carlo calculations were carried out using code MCNP4B2 (J. F. Briesmeister, Ed., "MCNP4B2—a general Monte Carlo N-particles transport code," Los Alamos National Laboratory Report LA-12625-M, Version 4A, 1997—incorporated herein by reference in its entirety) to design moderator of portable neutron generator-based PGNAA setup. Since portable neutron generator provides limited flux of 2.5 MeV neutrons, its moderator should has excellent efficiency with a of source-moderator-sample geometry. In order to optimize source-moderator-sample geometry of the system, thermal neutron intensity at the sample location is calculated for three different arrangements of source-moderator sample geometry shown in FIG. 1. FIG. 1A shows geometry for thermal neutron production at a cylindrical sample 4-1 (90 mm in diameter and 145 mm in height) by inserting a cylindrical high-density polyethylene (HDP) slab 1-1 between the portable neutron generator 3-1 and the sample 4-1.

Figure 1B:
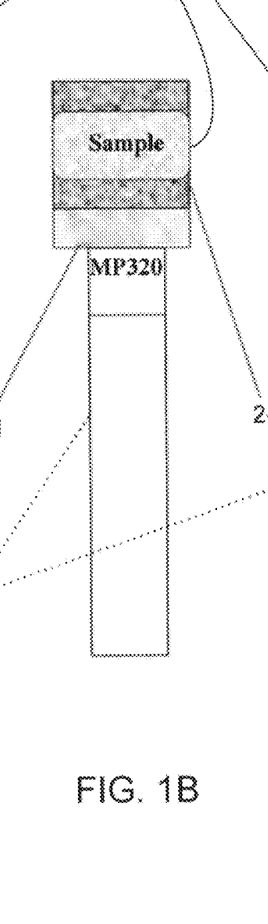
Figure 1C:
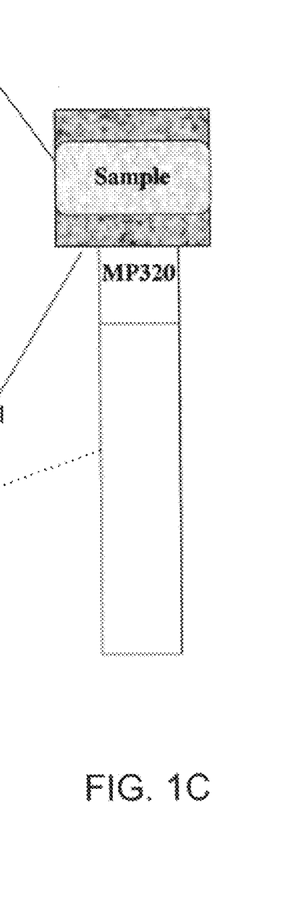

The HDP slab 1-1 has a diameter in the range of 10-30 cm, 12-28 cm, or 14-26 cm and its thickness varies in one cm steps and thermal neutron yield is calculated in sample volume for each slab thickness. Preferably, the HDP slab has a diameter of 25 cm. In another embodiment, as shown in FIG. 1B, a sample 4-1 is enclosed in a HDP cylinder 2-1 and placed after the HDP slab 1-1 with optimum thickness in the range of 1-10 cm, 3-9 cm, or 4-8 cm obtained from calculation of FIG. 1A. Preferably, the HDP slab 1-1 has a thickness of 6 cm. The outer diameter of the cylinder 2-1 was varied in equal steps and thermal neutron yield was calculated in sample volume for each outer diameter of the HDP cylinder 2-1. In another embodiment, the sample is enclosed in an HDP cylinder 2-1 and was placed next to neutron generator 3-1, as shown in FIG. 1C. The thermal neutron yield was calculated in the sample volume as a function of HDP cylinder 2-1 outer diameter.

Preferably, a system with the samples enclosed in the HDP cylinder and placed next to the neutron generator is used as the source-moderator in the configuration for the PGNAA apparatus.

Figure 2:
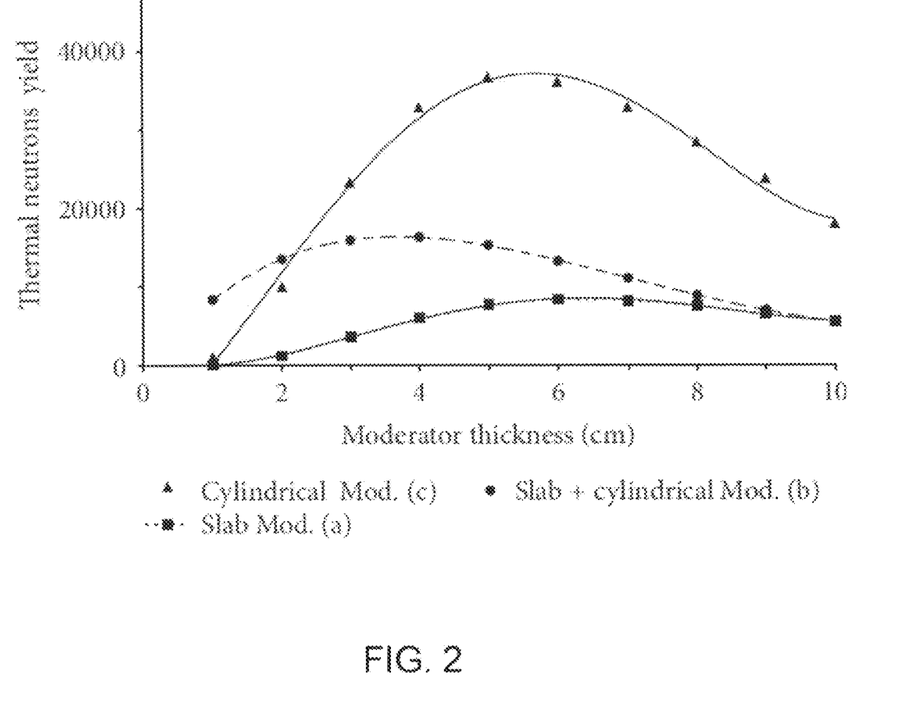
FIG. 2 is a graph demonstrating the thermal neutron yield at the sample location from the three sample geometries of the PGNAA setup.

FIG. 2 is a graph demonstrating the calculated yield of thermal neutron as a function of moderator thickness for the three different geometries of FIGS. 1A-1C. For the moderator cylinder, FIG. 2 moderator thickness has been obtained by subtracting cylinder constant inner diameter from the variable outer diameter.

The thermal neutron yield for the slab case (corresponding to the apparatus of FIG. 1A) increases with moderator thickness and reaches an increased value for 6 cm thick slab and then decreases primarily due to increasing distance from the neutron source. The decrease may also be caused due to increasing thermal neutron flux consumption in thermal neutron capture reaction in the increasing moderator material. As shown in FIG. 2, by enclosing the sample in HDP cylinder, the thermal neutron yield further increases with increasing thickness of the moderator, that is, increasing outer diameter of the cylinder. The neutron yield then decreases. As shown in FIG. 2, the maximum yield of thermal neutron in slab+cylinder (corresponding to the apparatus of FIG. 1B) configuration was obtained with a combination of slab thickness in the range of 1-10 cm, 3-9 cm, or 4-8 cm and HDP cylinder with an outer diameter in the range of 10-20 cm, 11-19 cm, or 12-18 cm. Preferably, the HDP cylinder has an outer diameter of 17 cm (4 cm wall thickness of the HDP cylinder). Preferably, the slab thickness is 6 cm. FIG. 2 also shows the thermal neutron yield for sample enclosed in the cylinder alone (corresponding to the apparatus of FIG. 1C). The yield increases with the cylinder outer diameter till it reaches a maximum value for HDP cylinder with outer diameter in the range of 15-25 cm, 16-24 cm, or 17-23 cm (corresponding to wall thickness in the range of 1-10 cm, 3-9 cm, or 4-8 cm of HDP cylinder. Preferably, the wall thickness is 6 cm). Preferably, the HDP cylinder has an outer diameter of 21 cm. With further increase in wall thickness of the cylinder, the thermal neutron intensity decreases, a trend similar to the ones observed for FIGS. 1A and 1B. The thermal neutron intensity obtained in FIG. 1C configuration was two times higher than the optimum values achieved from FIGS. 1A and 1B configurations. Therefore, the FIG. 1C configuration was chosen to design the moderator of the portable neutron generator-based PGNAA set.

Figure 3:
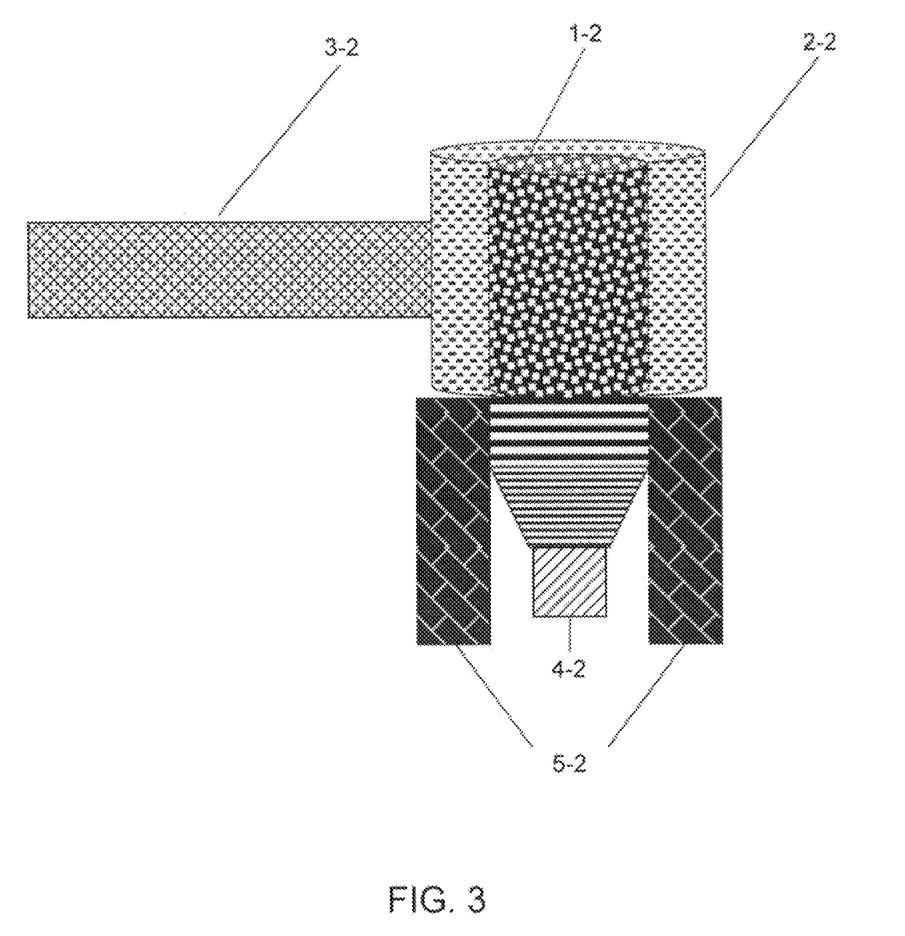
FIG. 3 is a schematic of the portable neutron generator based PGNAA setup.

FIG. 3 shows the schematic of the portable neutron generator based PGNAA setup. The PGNAA setup consists of a cylindrical specimen 1-2 container placed in a cylindrical cavity drilled through a cylindrical HDP moderator 2-2. A cylindrical gamma ray detector 4-2, with its longitudinal axis aligned along the sample's longitudinal axis, detects the prompt gamma rays from the sample. The moderator 2-2 is placed adjacent to portable neutron generator 3-2. In order to prevent undesired gamma ray and neutrons from reaching the detector, 3 mm thick lead shielding 5-2 and 50 mm thick neutron shielding surround the gamma ray detector. The neutron shielding is made of a mixture of paraffin and lithium carbonate mixed in equal weight proportions. The yield of nitrogen prompt gamma ray was calculated from proxy materials bulk sample, that is melamine, caffeine, urea, and disperse orange material samples. The elemental composition and masses of the samples are given in Table 1. Table 1 is presented below.

TABLE 1

Elemental composition of the bulk samples used in present study.

| Compound | Formula | Sample mass (g) | H (wt. %) | C (wt. %) | N (wt. %) | O (wt. %) |
|---|---|---|---|---|---|---|
| Melamine | $C_3H_6N_6$ | 682 | 4.8 | 28.6 | 66.7 | 0 |
| Urea | $CH_4N_2O$ | 816 | 6.7 | 20.0 | 46.7 | 26.7 |
| Caffeine | $C_8H_{10}N_4O_2$ | 580 | 5.2 | 49.5 | 28.6 | 16.5 |
| *Disperse orange | $C_{18}H_{14}N_4O_2$ | 534 | 4.4 | 67.9 | 17.6 | 10.1 |

*H, C, N, and O composition elements calculated for a sample containing 100% disperse orange.

The samples were contained in 90 mm diameter and 145 mm long plastic bottles. The intensity of a specific capture gamma ray of nitrogen is proportional to partial elemental cross-section due to capture of thermal neutrons in nitrogen, listed in Table 2 (H. D. Choi, R. B. Firestone, R. M. Lindstrom et al., *Database of Prompt Gamma Rays from Slow Neutron Capture for Elemental Analysis*, IAEA, 2007, http://wwwpu-b.iaea.org/MTCD/publications/ PDF/Pub1263web.pdf—incorporated herein by reference in its entirety). Table 2 is shown below.

TABLE 2

Capture gamma rays energies and partial elemental cross section in bismuth, germanium and nitrogen [20].

| Element | Gamma ray energy (keV) | $\sigma_\gamma^z(E_\gamma)$-barns |
|---|---|---|
| Bi | 162 | 0.008 |
|  | 320 | 0.0115 |
|  | 674 | 0.0026 |
|  | 2505 | 0.0021 |
|  | 2828 | 0.00179 |
|  | 4054 | 0.0137 |
|  | 4171 | 0.0171 |
| Ge | 175 | 0.164 |
|  | 493 | 0.133 |
|  | 500 | 0.162 |
|  | 596 | 1.100 |
|  | 608 | 0.250 |
|  | 868 | 0.553 |
|  | 961 | 0.129 |
|  | 1101 | 0.134 |
|  | 1204 | 0.141 |
|  | 1472 | 0.083 |
| N | 1678 | 0.0063 |
|  | 1885 | 0.0147 |
|  | 2000 | 0.0032 |
|  | 2520 | 0.0044 |
|  | 3532 | 0.0071 |
|  | 3678 | 0.0116 |
|  | 4508 | 0.0132 |
|  | 5269 | 0.0236 |
|  | 5297 | 0.0168 |
|  | 5533 | 0.0155 |
|  | 5562 | 0.0084 |
|  | 6322 | 0.0145 |
|  | 7298 | 0.0075 |
|  | 8310 | 0.0033 |
|  | 10829 | 0.0113 |

Figure 4:
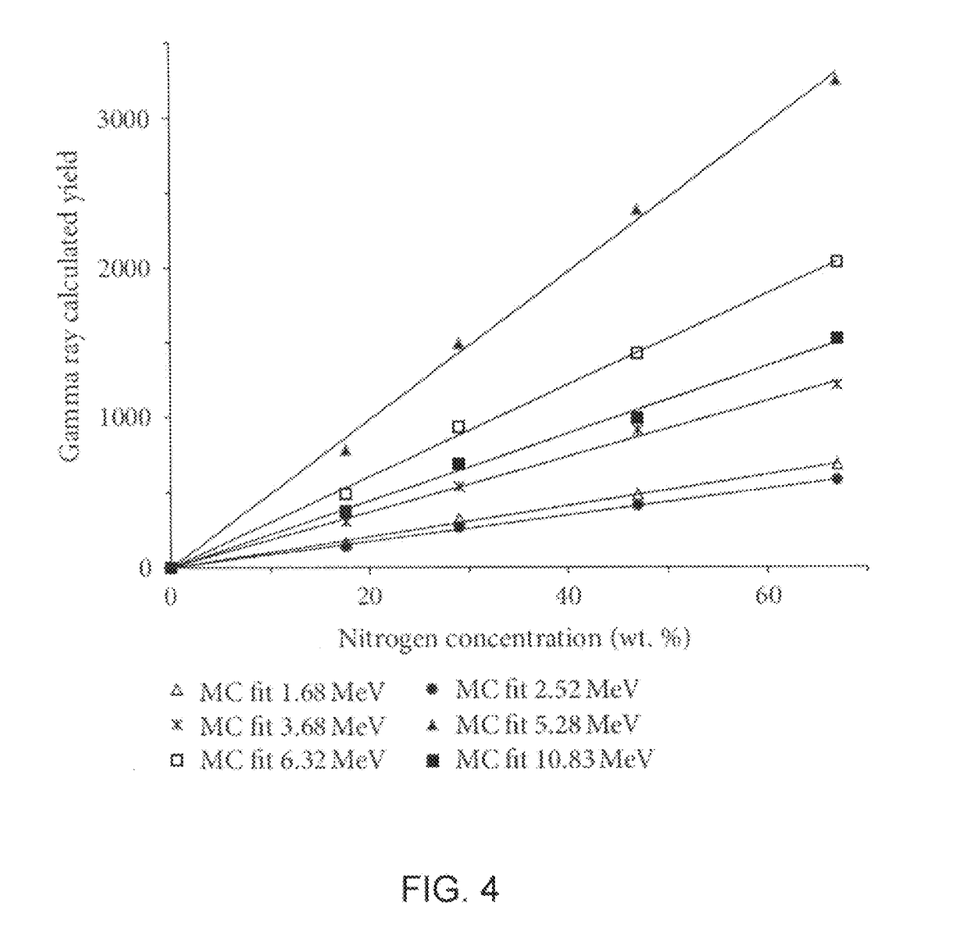
FIG. 4 is a graph of the gamma ray calculated yield plotted as a function of nitrogen concentration in various samples.

FIG. 4 shows calculated yield of 1.68, 2.52, 3.68, 5.28, 6.32, and 10.83 MeV nitrogen gamma rays as a function of nitrogen concentration in melamine, caffeine, urea, and disperse orange bulk samples. The calculated yield of 2.52 MeV prompt gamma rays from nitrogen was compared with the experimental yield of prompt gamma rays from the melamine, caffeine, urea, and disperse orange samples.

Nitrogen concentration in melamine, caffeine, urea, and disperse orange material samples was determined through their irradiation in the MP320 generator-based PGNAA setup shown in FIG. 3. A pulsed beam of 2.5 MeV neutrons was produced with 70 keV deuteron beam via (d, n) reaction using portable neutron generator. The portable neutron generator was operated with a pulsed deuteron beam with 5 milliseconds pulse width and 250 Hz beam frequency. The pulsed neutron beam improves the signal-to-background ratio in the PGNAA studies. The generator was operated at 70 µA deuteron beam current. The nitrogen prompt gamma ray yield data from the samples were acquired using a newly purchased 100 mm×100 mm (diameter×height) bismuth germinate (BGO) detector for a period of 3 to 4 hours per sample. BGO detector was chosen because it contains bismuth, which has smaller capture cross-section of thermal neutrons. Therefore, BGO detector is less sensitive to neutron radiation damage as compared to a NaI detector.

During the irradiation of the samples, the BGO detector, although well shielded, was also exposed to thermal neutrons and registered prompt gamma rays due to the capture of thermal neutrons in bismuth (Bi) and germanium (Ge) present in the BGO detector. The energies and intensities of prominent prompt gamma rays due to capture of thermal neutrons in detector and samples material are listed in Table 2.

Figure 5:
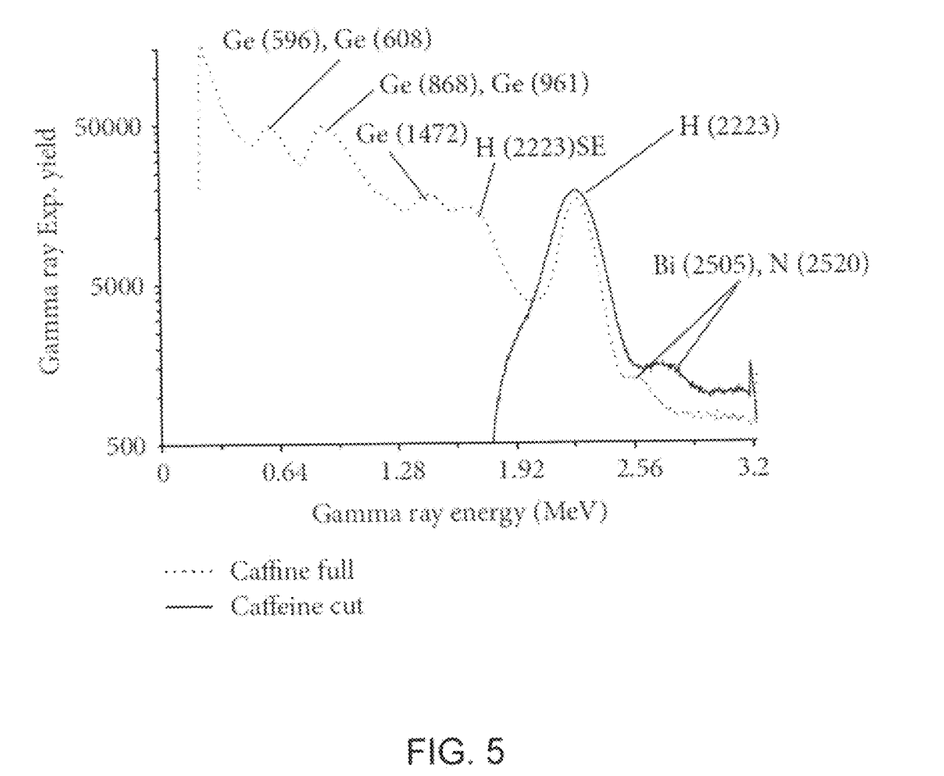
FIG. 5 is a graph of the prompt gamma ray experimental pulse height spectra from a caffeine sample.

FIG. 5 shows the prompt gamma ray experimental pulse height spectra from the caffeine sample over 1-3.22 MeV taken with the BGO detector. Also superimposed is the lower energy part suppressed caffeine sample pulse height spectrum.

Gamma ray spectra with energies less than 3.2 MeV energy were acquired. Nitrogen gamma rays with higher energies were not analyzed in this study because they were interfering with prompt gamma rays from the detector material. Further higher energies gamma rays have very poor statistics because photo absorption cross-section of gamma ray above 3 MeV energy decreases drastically due to competing Compton scattering and pair production reactions. This reduces detection probability of high energy gamma rays above 3 MeV gamma rays. Although intensity of 10 MeV nitrogen line is 2.6 times higher than 2.52 MeV line but the photoelectric cross-section drops by a factor of 300 from 2 to 10 MeV gamma gamma rays. This results in net reduction in detection efficiency of 10 MeV gamma rays using the BGO detector.

FIG. 5 shows BGO detector pulse height spectrum for caffeine sample over 0-3.22 MeV containing the 2.22 MeV hydrogen capture peak from the moderator material. Also shown in FIG. 5 is single escape (SE) peak associated with hydrogen capture full energy peak at 2223 keV. FIG. 5 further shows prompt gamma ray peaks at 596, 608, 868, 961, and 1472 due to thermal neutron capture in germanium in BGO detector material as was previously observed. Also shown in FIG. 5 are unresolved prompt gamma ray peaks from bismuth in BGO detector material and nitrogen in caffeine measured at 2.50 MeV and 2.52 MeV, respectively. Since the production cross-section of 2.52 MeV nitrogen gamma ray is two times higher than 2.50 MeV gamma ray of bismuth, nitrogen peak will still be measurable for samples containing nitrogen in quantities comparable with bismuth contents of the BGO detector.

Figure 6:
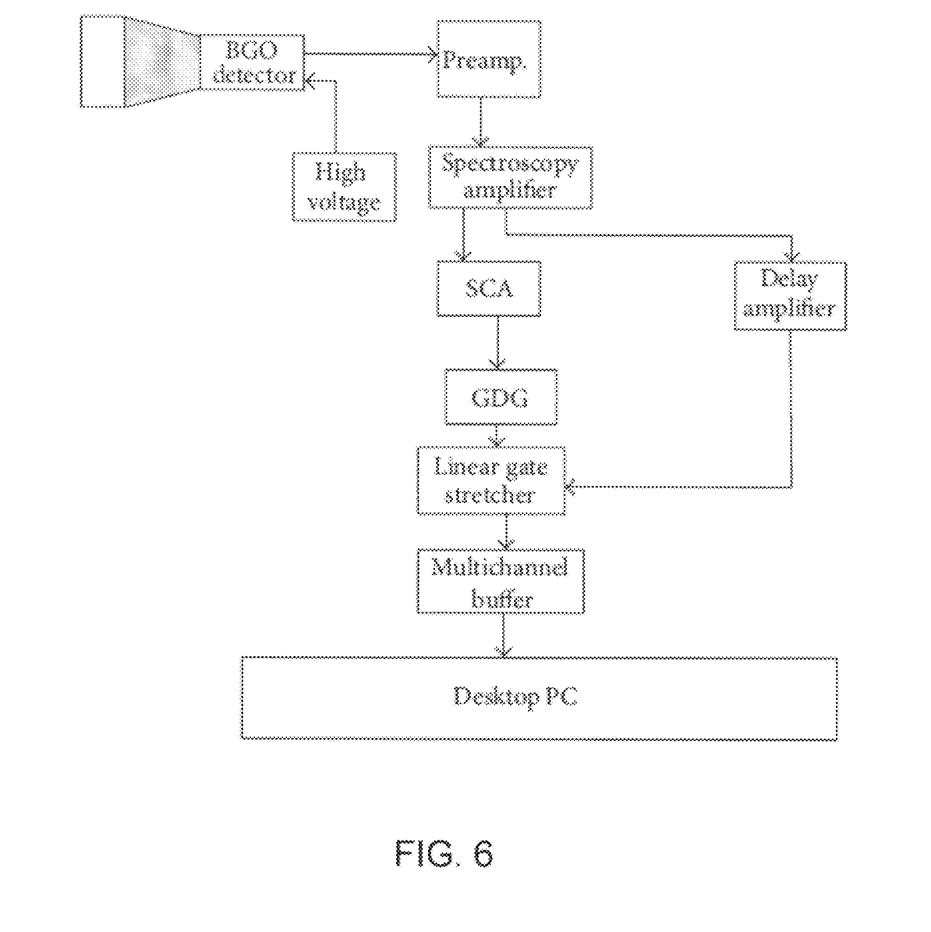
FIG. 6 is a block diagram of the BGO detector spectrum.

The nitrogen prompt gamma ray peak was located at the higher energy end of the pulse height spectrum. The count rate in the lower energy part of the spectrum was high and it was desired to suppress count rate in lower energy part of the spectrum to minimize detector dead time. The lower energy part of the pulse spectrum was suppressed (offset) using analogue standard NIM single-channel analyzer, gate and delay generator and linear gate circuitry shown in FIG. 6. FIG. 6 is an electronics block diagram used to suppress the lower energy part of the BGO detector spectrum. For data analysis purpose, each pulse height spectrum was converted into excel spectrum for later spectrum subtraction and peak integration. Also shown in FIG. 5 is caffeine sample pulse height spectrum with solid line after lower energy part of the spectrum is suppressed. In order to resolve the bismuth-nitrogen peaks from hydrogen 2.22 MeV peak, detector operating voltage was raised by 50 volts above its optimum operating voltage. Due to this effect, hydrogen peak shown with solid line is broader than the peak shown with dotted line and also bismuth-nitrogen peaks are more resolved from hydrogen 2.22 MeV peak than in the dotted line spectrum.

Figure 7:
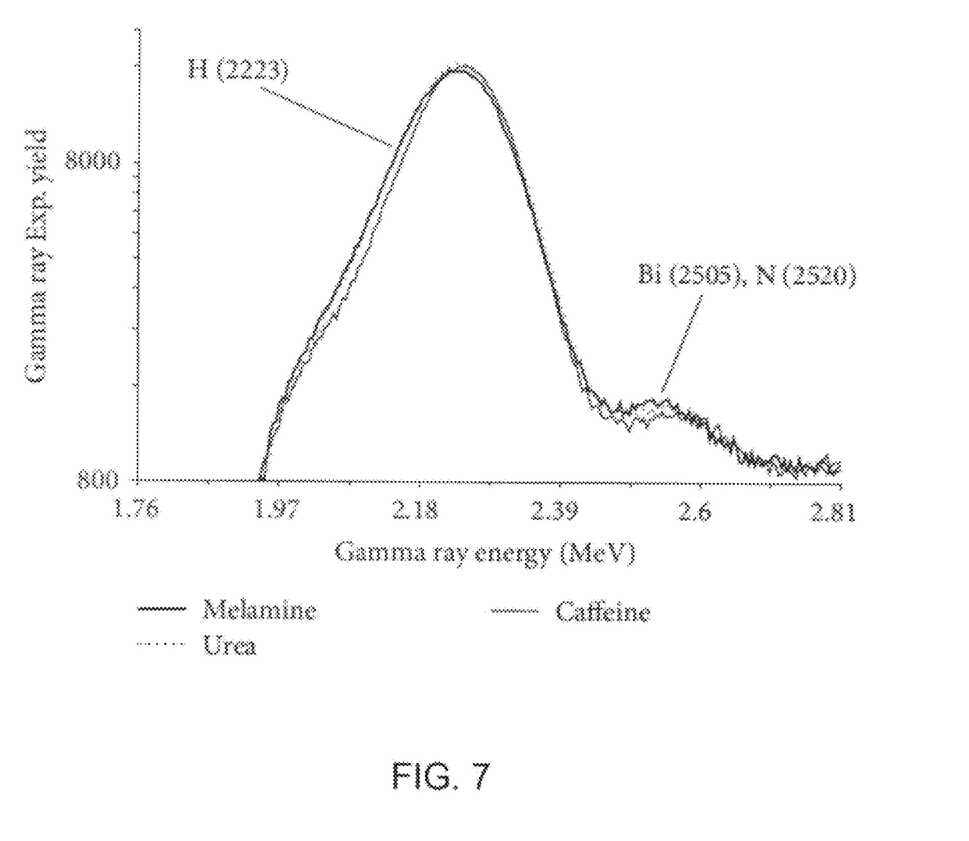
FIG. 7 is a graph of the prompt gamma ray experimental pulse height spectra of the BGO detector.
Figure 8:
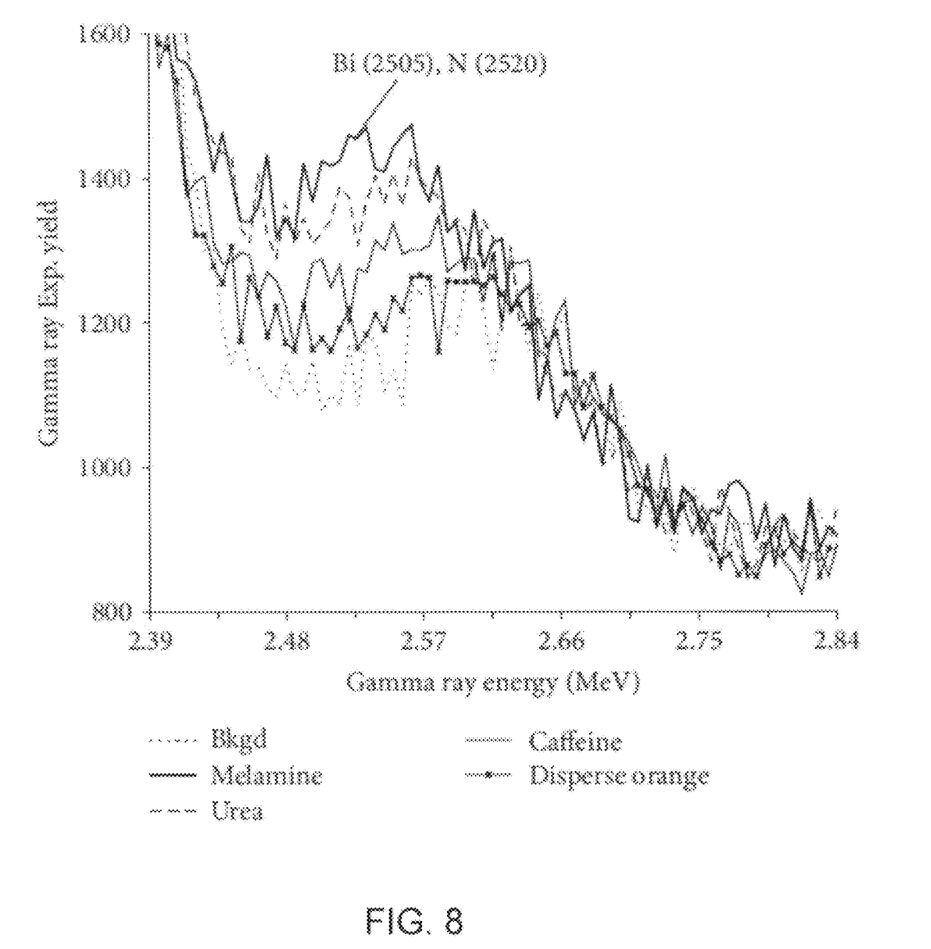
FIG. 8 is a graph of the unresolved 2.50 and 2.52 MeV bismuth and nitrogen prompt gamma ray experimental pulse height spectra of BGO detector from various samples.

FIG. 7 shows lower energy suppressed pulse height spectra of melamine, urea, and caffeine samples over 1.76-2.81 MeV showing hydrogen capture peak at 2.22 MeV along with unresolved prompt gamma ray peaks from bismuth and nitrogen at 2.50 and 2.52 MeV, respectively. FIG. 8 shows enlarged portion of FIG. 7 of 2.50 and 2.52 MeV bismuth and nitrogen prompt gamma ray experimental pulse height spectra of BGO detector over 2.39-2.84 MeV showing unresolved prompt gamma ray peaks from bismuth and nitrogen in melamine, urea, caffeine, and disperse orange superimposed upon background spectrum.

Since all samples have different matrix materials, it is difficult to find a common background sample material. Therefore a background spectrum was taken with an empty sample plastic container. Further water or polyethylene background sample are not suitable in this case because hydrogen contents of water or polyethylene background sample are higher than the actual samples and resulting background level around 2223 keV hydrogen capture peak in the background sample will be higher than actual spectrum. This will suppress the sample effects in the background subtracted spectra.

The nitrogen peaks have increasing trends depending upon their nitrogen concentration. The lowest nitrogen peak intensity has been measured for prompt gamma ray peak from disperse orange sample with 17.6 wt. % nitrogen and the highest nitrogen peak intensity has been observed for prompt gamma ray peak from melamine sample with 66.7 wt. % nitrogen concentration, as expected from data shown in Table 1. Finally, area under the normalized nitrogen peaks of melamine, urea, caffeine, and disperse orange samples was integrated and background was subtracted.

Figure 9:
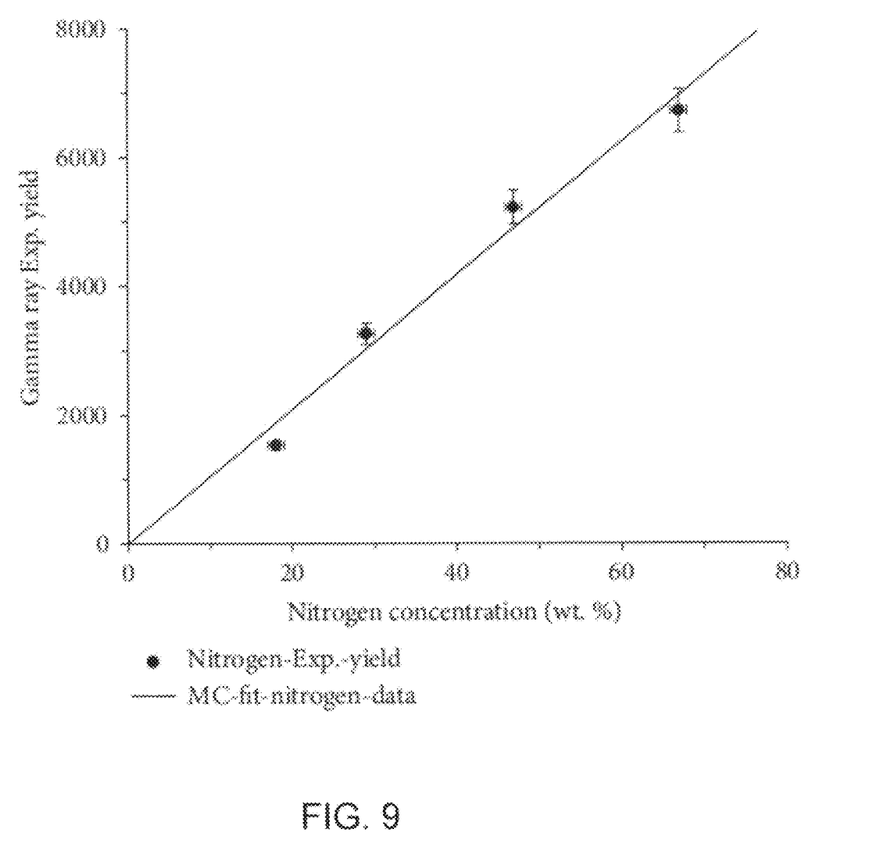
FIG. 9 is a graph of the experimental integrated yields of 2.52 MeV prompt gamma rays from nitrogen plotted as a function of nitrogen concentration in various samples.

The integrated yield of 2.52 MeV prompt gamma rays peak of nitrogen as a function of nitrogen concentration in caffeine, disperse orange, melamine, and urea samples is plotted in FIG. 9. The solid line in FIG. 9 represents the calculated yield of prompt gamma ray obtained from Monte Carlo calculations following the procedure described elsewhere. There is an excellent agreement between the theoretical yield and the experimental yield of nitrogen prompt gamma ray measured from melamine, urea, caffeine and disperse orange bulk samples using a portable neutron generator based PGNAA setup utilizing a 100 mm×100 mm (diameter×height) BGO detector. Preferably, the BGO is of a high density scintillation material with the chemical composition $Bi_4Ge_3O_{12}$ and can be machined to various shapes and geometries including cylinder-shaped detectors, block-shaped detectors, rectangular-shaped detectors, and parallel-epipedic-shaped detectors. More preferably, the BGO is a cylinder-shaped detector.

Finally the minimum detection limit of nitrogen concentration in proxy material samples MDC was calculated for the portable neutron-based PGNAA setup using the equation described elsewhere in detail (D. A. Gedcke, "How counting statistics controls detection limits and peak precession," ORTEC Application Notes AN59, 2001, http://www.ortec-online.com/—incorporated herein by reference in its entirety). The detection limit for an elemental concentration MDC measured under a peak with net counts NP and associated background counts NB under the peak is defined by the following:

$$MDC = 4.653*(C/N_P)*\sqrt{N_B}, \quad (1)$$

where C is the element's concentration in the peak corresponding to net counts NP. The corresponding error in MDC, that is, $\sigma MDC = (C/N_P)*[\sqrt{(2*N_B)}]$.

The MDC of nitrogen in proxy material samples for the KFUPM portable neutron generator was calculated to be 8.2±2.5 wt %. In spite of low thermal neutron flux of the portable neutron generator and low thermal capture cross-section of nitrogen, the value of MDC for nitrogen detection using a portable neutron generator is reasonable. The study has provided useful data for application of a portable D-D neutron generator in detection of nitrogen in bulk material samples.

In this study, a D-D portable neutron generator-based PGNAA system was tested for nitrogen concentration measurements in bulk samples. The PGNAA set up response was tested through 2.52 MeV nitrogen prompt gamma ray yield measurements from melamine, urea, caffeine, and disperse, orange bulk samples containing nitrogen over 17.6-66.7 wt %. In spite of low flux of thermal neutrons produced by D-D portable neutron generator and interference of 2.52 MeV gamma rays from nitrogen in bulk samples with 2.50 MeV gamma ray from bismuth in BGO detector material, an excellent agreement has been observed between the experimental and the calculated yield of nitrogen prompt gamma rays as a function of nitrogen concentration in melamine, urea, caffeine, and disperse orange bulk samples. This indicates the excellent performance of the portable neutron generator-based PGNAA setup for detection of elements with low thermal neutron capture cross-section.

In one embodiment of the invention, the PGNAA detector does not use an isotropic neutron source providing continuous radiation for the remote detection of nitrogen. The PGNAA detector is an accelerator based setup using 2.5 MeV neutrons.

In another embodiment, the PGNAA detector is not a fission neutron detector.

In another embodiment, the PGNAA detector is not a Deuterium-Tritium neutron generator using 14 MeV neutrons.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A bulk nitrogen detector for analysis of nitrogen by prompt gamma-ray neutron activation, comprising:
a sample cavity,
a portable D-D neutron generator having neutron tube,
a polyolefin moderator;
a BGO gamma ray detector; and
a neutron shield;
wherein the polyolefin moderator is positioned between the sample cavity and the neutron generator,
the BGO gamma ray detector is positioned orthogonally to the axis of the neutron tube on the sample cavity side of the polyolefin moderator, and
the neutron shield surrounds the BGO detector,
and wherein
the polyolefin moderator further comprises a cylindrical slab positioned between the portable neutron generator and the sample; or
the polyolefin moderator is a cylinder which encloses the sample cavity and is positioned adjacent to a high density polyethylene slab which is between the portable neutron generator and the cylinder; or
the polyolefin moderator is a high density polyethylene moderator cylinder which encloses the sample and is configured adjacent to the neutron generator.

2. The detector of claim 1, in which the apparatus is capable of detecting nitrogen in bulk samples.

3. The detector of claim 1 in which the portable D-D neutron generator is a pulsed D-D neutron generator.

4. The detector of claim 1, comprising a high density polyethylene slab in the form of a cylindrical shape having a diameter of 25 cm.

5. The detector of claim 1, wherein the polyolefin moderator is a high density polyethylene moderator cylinder which encloses the sample and is positioned adjacent to the neutron generator.

6. The detector of claim 1, in which the BGO gamma ray detector is a cylinder having a longitudinal axis aligned with the longitudinal axis of the sample cavity.

7. The detector of claim 1, further comprising:
a lead shield having a thickness of 3 mm;
wherein the neutron shield has a thickness of 50 mm; and
wherein the neutron shield is made of a mixture of paraffin and lithium carbonate mixed in equal weight proportions.

8. A method for detecting nitrogen in bulk samples, comprising:
exposing a nitrogen-containing sample in the sample cavity of the detector of claim 1 with neutrons generated by the portable D-D neutron generator, detecting prompt gamma rays emitted by the sample with the BGO gamma ray detector.

9. The detector of claim 1, wherein the polyolefin moderator further comprises a cylindrical slab positioned between the portable neutron generator and the sample.

10. The detector of claim 1, wherein the polyolefin moderator is a cylinder which encloses the sample cavity and is positioned adjacent to a high density polyethylene slab which is between the portable neutron generator and the cylinder.

11. The detector of claim 1, wherein the detector is not a deuteriumtritium neutron generator.

12. The detector of claim 1, wherein the moderator has a thickness of 1 to 10 cm.

13. The detector of claim 1, wherein the moderator has a thickness of 3 to 9 cm.

* * * * *